US011950847B1

(12) United States Patent
Moretti et al.

(10) Patent No.: US 11,950,847 B1
(45) Date of Patent: *Apr. 9, 2024

(54) PORTABLE MEDICAL DIAGNOSTICS DEVICE WITH INTEGRATED ARTIFICIAL INTELLIGENCE CAPABILITIES

(71) Applicant: AI Optics Inc., New York, NY (US)

(72) Inventors: Luke Michael Moretti, New York, NY (US); Andrew DiGiore, New York, NY (US)

(73) Assignee: AI Optics Inc., New York, NY (US)

( * ) Notice: Subject to any disclaimer, the term of this patent is extended or adjusted under 35 U.S.C. 154(b) by 593 days.

This patent is subject to a terminal disclaimer.

(21) Appl. No.: 17/211,166

(22) Filed: Mar. 24, 2021

Related U.S. Application Data

(60) Provisional application No. 63/035,268, filed on Jun. 5, 2020, provisional application No. 62/994,202, filed on Mar. 24, 2020.

(51) Int. Cl.
*A61B 3/12* (2006.01)
*A61B 3/00* (2006.01)
*G06N 3/08* (2023.01)

(52) U.S. Cl.
CPC .......... *A61B 3/1208* (2013.01); *A61B 3/0008* (2013.01); *A61B 3/0025* (2013.01); *A61B 3/0041* (2013.01); *G06N 3/08* (2013.01)

(58) Field of Classification Search
CPC ... A61B 3/1208; A61B 3/0008; A61B 3/0025; A61B 3/0041; G06N 3/08
See application file for complete search history.

(56) References Cited

U.S. PATENT DOCUMENTS

| | | | |
|---|---|---|---|
| 5,912,720 | A | 6/1999 | Berger |
| 8,687,862 | B2 | 4/2014 | Hsu |
| 9,757,031 | B2 | 9/2017 | Wang |
| 10,376,142 | B2 | 8/2019 | Dirghangi |

(Continued)

FOREIGN PATENT DOCUMENTS

| | | |
|---|---|---|
| JP | 2020178903 | 11/2020 |
| KR | 20190091857 | 8/2019 |

(Continued)

OTHER PUBLICATIONS

Center for Innovation (L V Prasad Eye Institute), Open Indirect Ophthalmoscope, https://lvpmitra.com/oio#introduction (2021).

(Continued)

*Primary Examiner* — James C. Jones
(74) *Attorney, Agent, or Firm* — Knobbe, Martens, Olson & Bear LLP

(57) ABSTRACT

A handheld, portable devices with integrated artificial intelligence (AI) configured to assess a patient's body part to detect a disease and methods of operating such devices are disclosed. In some cases, a device can be a retina camera configured to assess a patient's retina and, by using an on-board AI retinal disease detection system, provide real-time analysis and diagnosis of the patient's retina. Easy and comfortable visualization of the patient's retina can be facilitated using such retina camera, which can be placed over the patient's eye, display the retina image on a high-resolution display, analyze a captured image by the on-board AI system, and provide determination of presence of a disease.

21 Claims, 4 Drawing Sheets

(56) References Cited

U.S. PATENT DOCUMENTS

| | | |
|---|---|---|
| 2005/0234300 A1 | 10/2005 | Farrell |
| 2011/0299036 A1 | 12/2011 | Goldenholz |
| 2012/0257163 A1 | 10/2012 | Dyer |
| 2018/0055357 A1 | 3/2018 | Meyerson |
| 2018/0153399 A1 | 6/2018 | Fink |
| 2019/0133435 A1 | 5/2019 | Browne |
| 2019/0216308 A1 | 7/2019 | Senaras et al. |
| 2020/0170564 A1 | 6/2020 | Jiang |
| 2020/0196869 A1* | 6/2020 | Narayanan ............ A61B 5/7246 |
| 2020/0405148 A1 | 12/2020 | Tran |
| 2021/0035301 A1 | 2/2021 | Soares |
| 2022/0405927 A1* | 12/2022 | Villard ................. A61B 3/0008 |

FOREIGN PATENT DOCUMENTS

| | | |
|---|---|---|
| KR | 102032193 | 10/2019 |
| KR | 20190129247 | 11/2019 |
| WO | WO 2016/179370 | 11/2016 |
| WO | WO 2017/031099 | 2/2017 |
| WO | WO 2020/173516 | 9/2020 |

OTHER PUBLICATIONS

Bleicher, Ariel, Teenage Whiz Kid Invents an AI System to Gianose her Grandfather's Eye Disease, IEEE Spectrum (2017). https://spectrum.ieee.org/the-human-os/biomedical/diagnostics/teenage-whiz-kid-invents-an-ai-system-to-diagnose-her-grandfathers-eye-disease.

Masumoto, et al., Deep-learning classifier with an ultrawide-field scanning laser ophthalmoscope detects glaucoma visual field severity, Glaucoma Journal 27(7):647-652 (2018).

Ting, et al., Artificial intelligence and deep learning in ophthalmology, Br J. Ophthalmol 103:167-175 (2019).

WelchAllyn Standard Ophthalmoscope (https://www.welchallyn.com/en/products/categories/physical-exam/eye-exam/ophthalmoscopes--traditional-direct/35v_standard_ophthalmoscope.html#_) 2018.

WelchAllyn PanOptic Brochure (2016).

WelchAllyn iExaminer (https://www.welchallyn.com/en/microsites/iexaminer.html) 2018.

D-Eye Smartphone-Based Retinal Imaging System (https://www.d-eyecare.com/en_US/product#features) (retrieved in Mar. 2021).

Horus 100 fundus camera (http://www.miis.com.tw/product01.php?no=36) 2014.

Horus 200 portable fundus camera (http://www.miis.com.tw/product01.php?no=84) 2014.

Microclear Luna Fundus Camera (https://www.microcleartech.com/en/productInfo?p=hfc_v2) (retrieved in Mar. 2021).

Mediworks FC 161 hand-held fundus camera (https://www.mediworks.biz/en/product/handheld-fundus-camera-fc161).

Remidio NMFOP (https://www.remidio.com/fop.php) (retrieved in Mar. 2021).

Welch Allyn RetinaVue 700 Imager (2019).

IDx-DR Autonomous AI (https://dxs.ai/products/dermatology/autonomous-ai/) 2020.

IDx-DR Overview: Close Care Gaps, Prevent Blindness (https://dxs.ai/products/idx-dr/idx-dr-overview/) 2020.

EyeNuk EyeArt screening system (https://www.eyenuk.com/en/) (retrieved in Mar. 2021).

\* cited by examiner

PORTABLE MEDICAL DIAGNOSTICS DEVICE WITH INTEGRATED ARTIFICIAL INTELLIGENCE CAPABILITIES

CROSS-REFERENCE TO RELATED APPLICATIONS

The present application claims the benefit of U.S. Provisional Application No. 62/994,202 filed on Mar. 24, 2020 and U.S. Provisional Application No. 63/035,268 filed on Jun. 5, 2020, each of which is incorporated by reference in its entirety.

TECHNICAL FIELD

Disclosed are portable medical diagnostics devices that can have integrated artificial intelligence (AI) capabilities.

BACKGROUND

A fundus (or retina) camera is an instrument for inspecting the retina of the eye. Many ophthalmologic, neurologic, and systemic diseases can cause structural abnormalities in the retina, which alter the visual appearance of the retina. These structural and visible abnormalities are known as biomarkers, and they may indicate the presence of a disease. For example, diabetics have high levels of circulating blood sugar that, over time, can cause damage to the small vessels in the retina and lead to the formation of microaneurysms. Such microaneurysms indicate the presence of diabetic retinopathy. Clinicians use fundus cameras to visualize and assess a patient's retina for biomarkers in order to diagnose the disease. Therefore, it is desirable for a fundus camera to produce an adequate view of the retina in order for sufficient visualization and disease diagnosis. Given the importance of the appearance of the retina in disease diagnosis, improvements in ophthalmoscopy and retinal image analysis can thus be beneficial.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

SUMMARY

Figure 1:
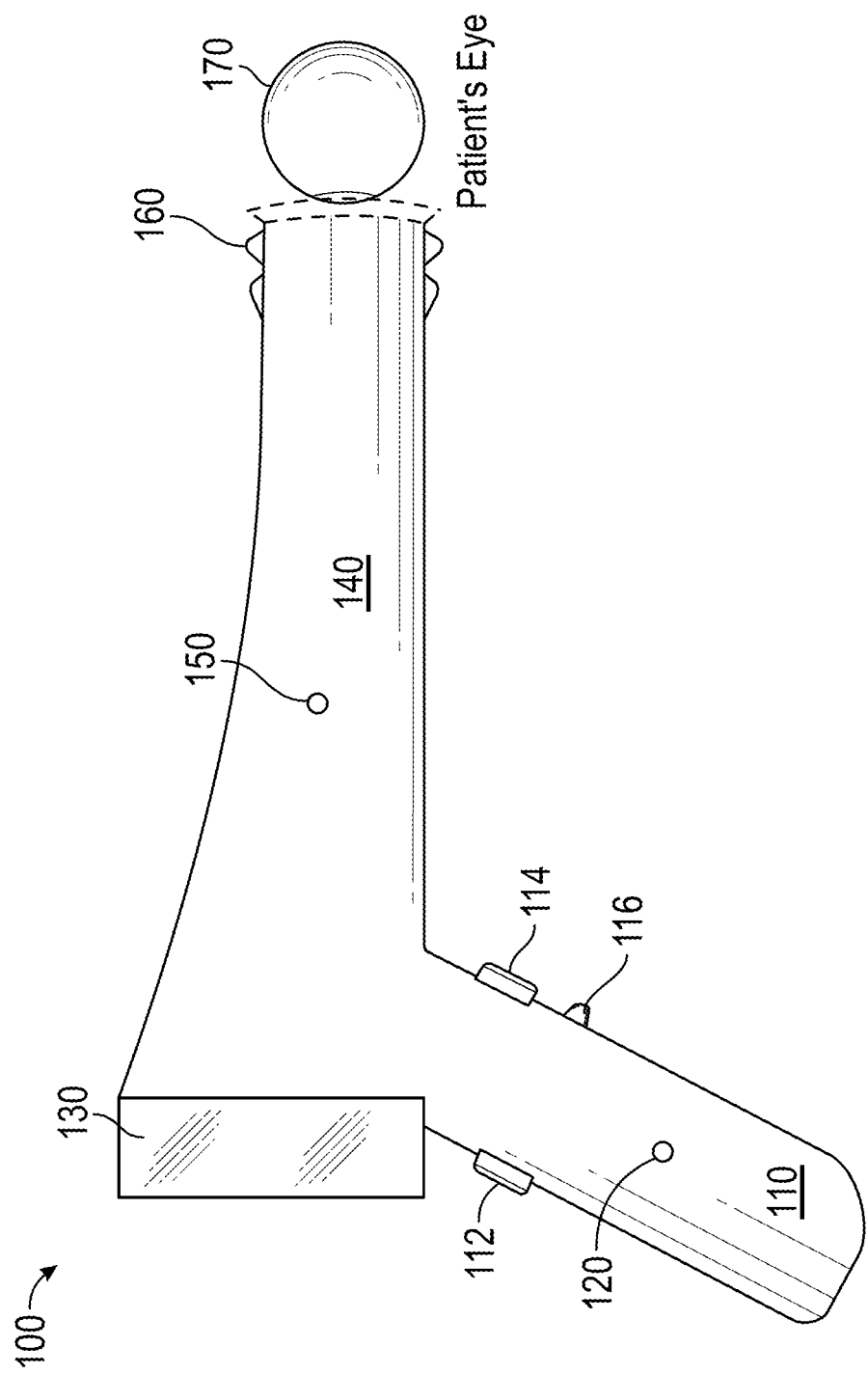
FIG. 1 illustrates a retina camera.

A portable medical diagnostics device can include a housing comprising a body and a handle, the handle connected to the body and configured to be held by a user, a display at least partially supported by the housing, a light source supported by the housing, the light source configured to irradiate a body part of a patient with light, imaging optics supported by the housing, the imaging optics configured to receive light reflected by the body part, an image detector array configured to receive light from the imaging optics and to sense the received light, and electronic processing circuitry supported by the housing. The electronic processing circuitry can be configured to generate at least one image of the body part based on signals received from the image detector array, display the at least one image on the display, process the at least one image with a machine learning model to determine presence of at least one disease from a plurality of diseases that the machine learning model has been trained to identify, and provide a determination of the presence of the at least one disease on the display. The electronic processing circuitry can process the at least one image and provides the determination of the presence of the at least one disease without requiring network connectivity The portable medical diagnostics device of the preceding paragraph and/or any of the diagnostics devices disclosed herein can include any combination of the one or more features disclosed herein. Methods of operating the portable medical diagnostics device of the preceding paragraph and/ or any of the diagnostics devices disclosed herein are provided.

DETAILED DESCRIPTION

Introduction

A handheld, portable device (or instrument) with integrated artificial intelligence (AI) can be used to assess patient's body part to detect a disease. For example, the device can be a retina camera configured to assess a patient's eye (or retina) and, by using an on-board AI retinal disease detection system, provide real-time analysis and diagnosis of disease that caused changes to the patient's retina. Easy and comfortable visualization of the patient's retina can be facilitated using such retina camera, which can be placed over the patient's eye, display the retina image on a high-resolution display, potentially with screenshot capabilities, analyze at least one captured image by the on-board AI system, and provide determination of presence of a disease.

Such retina camera can perform data collection, processing, and diagnostics tasks on-board without the need to connect to another computing device or Internet service. This approach can avoid potential interruptions of the clinical workflow when using cloud-based solutions, which involve transfer of data over the network and, accordingly, rely on network connectivity. Such retina camera can potentially improve accuracy (for instance, as compared to fundus cameras that rely on a human to perform analysis), facilitate usability (for example, because no connectivity is used to transfer data for analysis or transfer results of the analysis, because the device may be intuitive and easy to use, etc.), provide diagnostic results in real-time, facilitate security and guard patient privacy (for example, because data is not transferred to another computing device), or the like. Such retina camera can be used in many settings, including places where network connectivity is unreliable or lacking.

Such retina camera can allow for better data capture and analysis, facilitate improvement of diagnostic sensitivity and specificity, and improve disease diagnosis in patients. Existing fundus cameras may lack one or more of portability, display, on-board AI capabilities, etc. or require one or more of network connectivity for sharing data, another device (such as, mobile phone or computing device) to view collected data, rigorous training of the user, etc. In contrast, allowing for high-quality retinal viewing and image capturing with better, faster analysis and detection of the presence of disease via on-board AI system (sometimes referred to as AI system) and image-sharing capabilities, the retina cameras described herein can potentially provide improved functionality, utility, and security. Such retina camera can be used in hospitals, clinics, and/or at home. The retina cameras or other instruments described herein, however, need not include each of the features and advantages recited herein but may possibly include any individual one of these features and advantages or may alternatively include any combination thereof.

To allow the AI system to operate on-board the retina camera, the retina camera may implement one or more techniques for reducing the size of the AI system (or of machine learning model(s)) or for reducing the amount of processing power required to run the AI system (or machine learning model(s)). These techniques can include reducing the computational cost and optimizing for power and memory consumption. More specifically, these techniques include, but are not limited to, one or more of: training one or more machine learning models on a custom-built shallow neural network, which may include any number of layers, such as a single layer neural network (as this may achieve similar performance to larger networks, but with less complexity), using alternate neural networks with streamlined architecture that use depth-wise separable convolutions (such as, depth-wise separable convolutional networks) to build light-weight deep neural networks, using networks with fewer parameters, pruning (or removing) unused layers from the neural network, which can be a convolutional neural network (for example, by removing one or more of weights or nodes), quantizing network weights and/or activation layers (or functions), or using model optimization toolkits. In some cases, pruning one or more nodes or layers may be preferable because doing so can optimize (such as, reduce) the model size.

In contrast, AI-based medical image analysis systems that require connectivity (such as, cloud-based systems) tend to be large and require significant processing power to execute tasks. These devices cannot simply be ported from the cloud and ran on portable hardware systems, such as any of the portable medical diagnostics devices described herein, because of the many challenges posed by the limited power, computing resources, and memory available on portable devices. Therefore, it is a challenge to run a complex model using deep learning neural networks for image classification (such as, retinal image classification) on a handheld portable device. In addition, it is also a challenge to design an AI system (or machine learning models) to process one or more images quickly (such as, in real-time) on a portable device with limited processing power. The disclosed devices overcome these challenges.

As another example, the device can be an otoscope configured to assess a patient's ear and, by using an on-board artificial intelligence (AI) ear disease detection system, possibly provide immediate analysis and/or diagnosis of diseases of the patient's ear. Such an otoscope can have one or more advantages described above or elsewhere in this disclosure. As yet another example, the device can be a dermatology scope configured to assess a patient's skin and, by using an on-board artificial intelligence (AI) skin disease detection system, possibly provide immediate analysis and/or diagnosis of diseases of the patient's skin. Such a dermatology scope can have one or more advantages described above or elsewhere in this disclosure.

Various aspects of the disclosure will now be described with regard to certain examples and embodiments, which are intended to illustrate but not limit the disclosure.

Retina Camera with On-Board AI

FIG. 1 illustrates an example retina camera 100. A housing of the retina camera 100 can include a handle 110 and a body 140 (in some cases, the body can be barrel-shaped). The handle 110 can optionally support one or more of power source, imaging optics, or electronics 120. The handle 110 can also possibly support one or more user inputs, such as a toggle control 112, a camera control 114, an optics control 116, or the like. Toggle control 112 may be used to facilitate operating a display 130 in case of a malfunction. For example, toggle control 112 can facilitate manual scrolling of the display, switching between portrait or landscape mode, or the like. Toggle control 112 can be a button. Toggle control 112 can be positioned to be accessible by a user's thumb. Camera control 114 can facilitate capturing at least one image. Camera control 114 can be a button. Camera control 114 can be positioned to be accessible by a user's index finger (such as, to simulate action of pulling a trigger) or middle finger. Optics control 116 can facilitate adjusting one or more properties of imaging optics, such as illumination adjustment, aperture adjustment, focus adjustment, zoom, etc. Optics control 116 can be a button or a scroll wheel. For example, optics control 116 can focus the imaging optics. Optics control 116 can be positioned to be accessible by a user's middle finger or index finger.

The retina camera 100 can include the display 130, which can be a liquid crystal display (LCD) or other type of display. The display 130 can be supported by the housing as illustrated in FIG. 1. For example, the display 130 can be positioned at a proximal end of the body 140. The display 130 can be one or more of a color display, high resolution display, or touch screen display. The display 130 can reproduce one or more images of the patient's eye 170. The display 130 can allow the user to control one or more image parameters, such as zoom, focus, or the like. The body 140 can support one or more of the power source, imaging optics, imaging sensor, electronics 150 or any combination thereof.

A cup 160 can be positioned on (such as, removably attached to) a distal end of the body 140. The cup 160 can be made at least partially from soft and/or elastic material for contacting patient's eye orbit to facilitate examination of patient's eye 170. For example, the cup can be made of plastic, rubber, rubber-like, or foam material. Accordingly, the cup 160 may be compressible. The cup 160 can also be disposable or reusable. In some cases, the cup 160 can be sterile. The cup 160 can facilitate one or more of patient comfort, proper device placement, blocking ambient light, or the like. Some designs of the cup may also assist in establishing proper viewing distance for examination of the eye and/or pivoting for panning around the retina.

Figure 2:
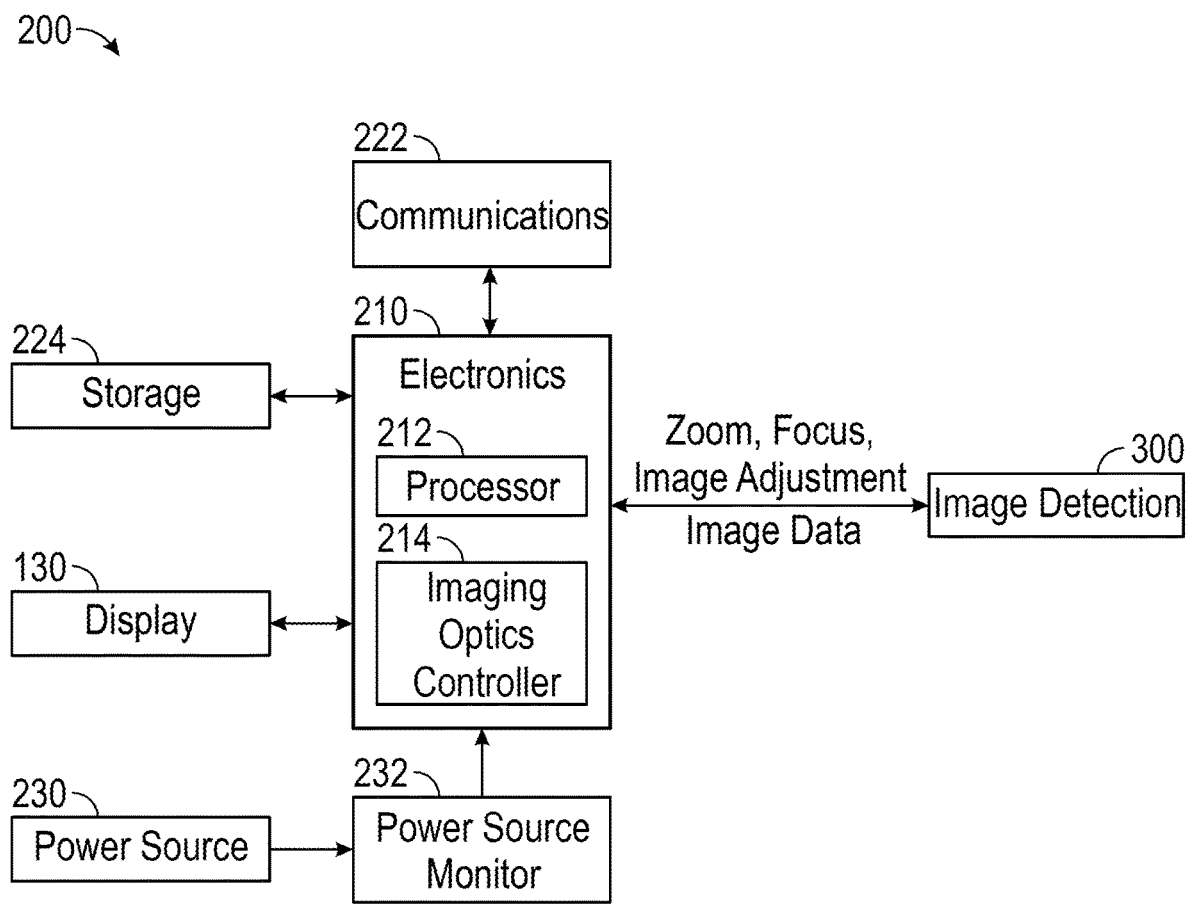
FIG. 2 schematically illustrates a system level diagram showing retina camera components of FIG. 1.

FIG. 2 illustrates a block diagram 200 of various components of the retina camera 100. Power source 230 can be configured to supply power to electronic components of the retina camera 100. Power source 230 can be supported by the handle 110, such as positioned within or attached to the handle 110 or be placed in another position on the retina camera 100. Power source 230 can include one or more batteries (which may be rechargeable). Power source 230 can receive power from a power supply (such as, a USB power supply, AC to DC power converter, or the like). Power source monitor 232 can monitor level of power (such as, one or more of voltage or current) supplied by the power source 230. Power source monitor 232 can be configured to provide one or more indications relating to the state of the power source 230, such as full capacity, low capacity, critical capacity, or the like. One or more indications (or any indications disclosed herein) can be visual, audible, tactile, or the like. Power source monitor 232 can provide one or more indications to electronics 210.

Electronics 210 can be configured to control operation of the retina camera 100. Electronics 210 can include one or more hardware circuit components (such as, one or more controllers or processors 212), which can be positioned on one or more substrates (such as, on a printed circuit board). Electronics 210 can include one or more of at least one graphics processing unit (GPU) or at least one central processing unit (CPU). Electronics 210 can be configured to operate the display 130. Storage 224 can include memory for storing data, such as image data obtained from the patient's eye 170, one or more parameters of AI detection, or the like. Any suitable type of memory can be used, including volatile or non-volatile memory, such as RAM, ROM, magnetic memory, solid-state memory, magnetoresistive random-access memory (MRAM), or the like. Electronics 210 can be configured to store and retrieve data from the storage 224.

Communications system 222 (sometimes referred to as an interface) can be configured to facilitate exchange of data with another computing device (which can be local or remote). Communications system 222 can include one or more of antenna, receiver, or transmitter. In some cases, communications system 222 can support one or more wireless communications protocols, such as WiFi, Bluetooth, NFC, cellular, or the like. In some instances, the communications system can support one or more wired communications protocols, such as USB. Electronics 210 can be configured to operate communications system 222. Electronics 210 can support one or more communications protocols (such as, USB) for exchanging data with another computing device.

Electronics 210 can control an image detection system 300, which can be configured to facilitate capturing of (or capture) image data of the patient's eye 170. Electronics 210 can control one or more parameters of the image detection system 300 (for example, zoom, focus, aperture selection, image capture, provide image processing, or the like). Such control can adjust one or more properties of the image of the patient's eye 170. Electronics 210 can include an imaging optics controller 214 configured to control one or parameters of the image detection system 300. Imaging optics controller 214 can control, for example, one or more motor drivers of the image detection system 300 to drive motors (for example, to select an aperture, to select lenses that providing zoom, to move of one or more lenses to provide autofocus, to move a detector array 380 or image sensor to provide manual focus or autofocus, or the like). Control of one or more parameters of the image detection system 300 can be provided by one or more of user inputs (such as a toggle control 112, a camera control 114, an optics control 116, or the like), display 130, etc. Image detection system 300 can provide image data (which can include one or more images) to electronics 210. As disclosed herein, electronics 210 can be supported by the retina camera 100. The electronics 210 may not be configured to be attached to (such as, connected to) another computing device (such as, mobile phone or server) to perform determination of presence of a disease.

Figure 3:
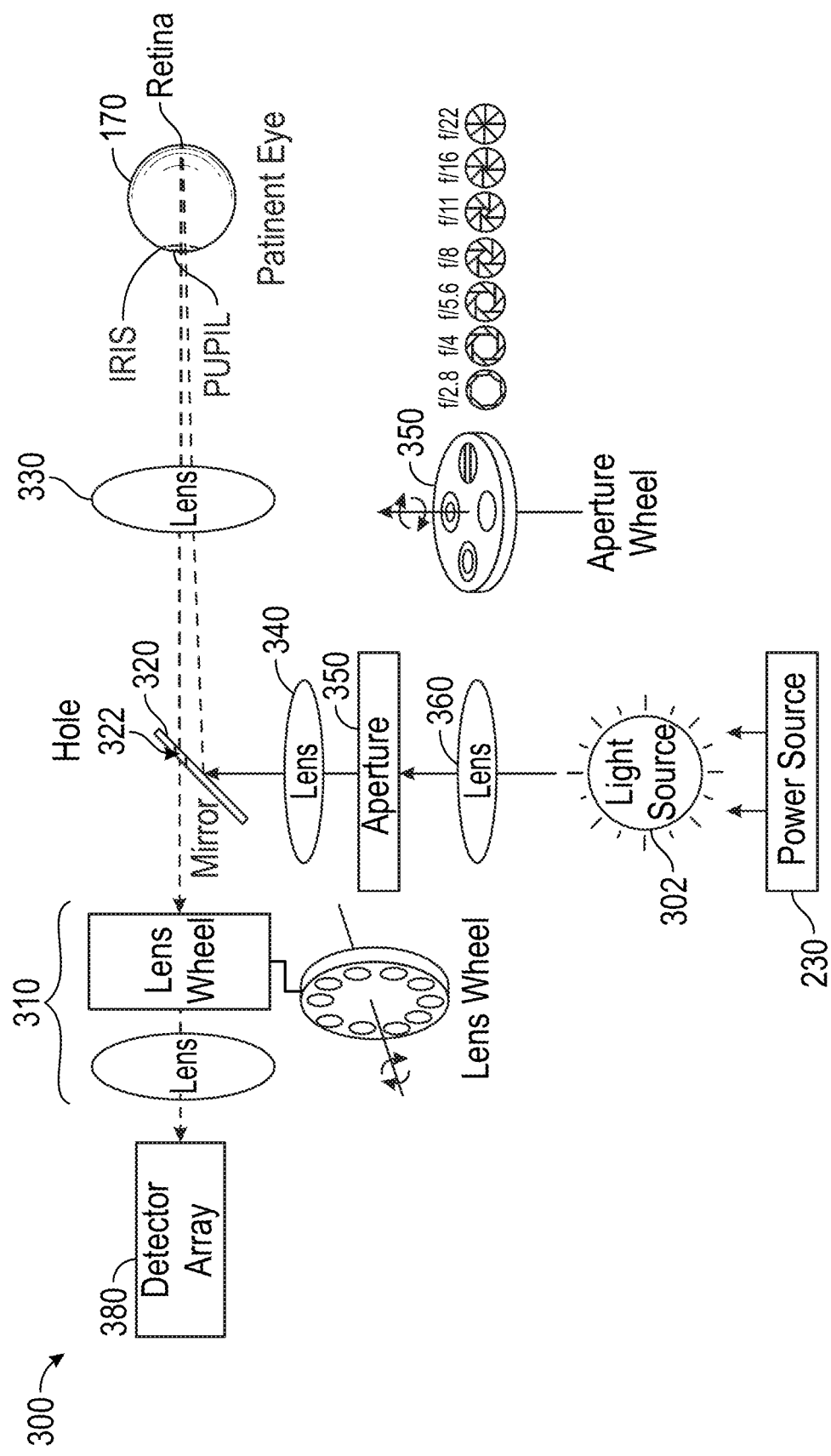
FIG. 3 schematically illustrates an optical path through an image detection system of the retina camera of FIG. 1.

FIG. 3 illustrates a block diagram of the image detection system 300. A light source 302, which can be powered by the power source 230, can generate light for transmission into and illumination of the patient's eye 170. The light source 302 can include one or more of emitters comprising, for example, one or more light emitting diode(s) or incandescent bulbs. Different light emitters having different properties such as different spectral characteristic (e.g., different colors or wavelength distributions) can be provided to offer the user a selection of different types of illumination. For example, the light source 302 can provide one or more of visible light (for example, white light, blue light, red light, green light), infrared light, or the like using one or more emitters. Selection of the type of light provided by the light source 302 can be performed via the optics control 116 which may control activation and/or intensity level of the one or more emitters. Optical paths from different light sources can be combined with one or more beam combiner (e.g., dichroic reflector, beam splitter, etc.). The light source 302 may be changed (for example, by the optics control 116), during various portions of the image capture procedure. For example, the light source 302 can provide infrared light during a live video preview mode prior to image capture, and be changed to visible light for image capture. The light source 302 may also be cycled through different types of light, such as infrared light and then visible light, in order to capture images with multiple types of illumination. The detector array 380 is also included in the system to provide images of the patient's eye 170 that is illuminated with the light source 302.

Accordingly, the illustrated in FIG. 3, the image detection system 300 can optionally include two optical paths, a first optical path from the light source 302 to the eye 170 of the patient or subject being evaluated, and a second optical path from the patient or subject's eye to the detector array 380. Optionally, lens 360 can be included in the first optical path after the light source 302 to collect light from the light source. In some designs, lens 360 provides beam-shaping possibly increasing collimation of light generated by the light source 302, for example, collimating light source 302 the into a beam. Aperture wheel (or a fixed aperture) 350 can be positioned in the first optical path after the lens 360 such that lens 360 is between light source 302 and the aperture wheel. Aperture wheel 350 can include one or more apertures of different sizes and/or shapes (as illustrated in FIG. 3) that allow the light to pass therethrough. Additionally or alternatively, aperture wheel 350 can adjust the size of an aperture (as illustrated in FIG. 3) and thus control the amount of light passed therethrough. In some cases, one or more apertures are circular. Selection of the suitable aperture can be performed via the optics control 116. Aperture wheel 350 can be controlled by a motor driver such that light from the light source passes through the selected aperture to the patient's eye 170. Alternatively, the aperture 350 may be fixed. Optionally, lens 340 can be positioned in the first optical path after the aperture wheel or fixed aperture 350. Accordingly, the aperture wheel (or fixed aperture) 350 and/or lens 360 may be in the first optical path between the light source 302 and lens 340. Lens 340 can potentially aid in focusing the light onto the eye after it has passed through an aperture.

Reflector 320 can be in the first optical path after the lens 340. Likewise, any of lens 360, aperture wheel (or fixed aperture) 350, and lens 340 may be disposed in the first optical path between the detector array 380 and the reflector 320. Reflector 320 can be configured to direct light into the patient's eye 170 so as to illuminate the retina. Reflector 320 can include a mirror (such as 45° mirror), prism, beamsplitter, or the like. Optionally, lens 330 can be positioned after the reflector 320 in the first optical path between the reflector and the patient's eye 170. In some implementations, lens 330 can be configured to focus the light from the reflector 320 onto the retina.

Accordingly, light from the light source 302 can illuminate the retina of the patient's eye 170 and be reflected. Light reflected from the eye can propagate along the second optical path to the detector array 380. Note that the first and second optical paths may potentially overlap, for example, from the eye to the reflector 320. In some designs, for example, lens 330 and/or the reflector 320 by be included in both the first and second optical paths. Accordingly, light reflected from the eye 170 can pass through the lens 330, which can collect the reflected light possibly increasing collimation of the reflected light from the retina for example, possibly collimating the light reflected into a beam. Light transmitted through lens 330 is show in the image detection system 300 depicted in FIG. 3 as incident on reflector 320 and transmitted therethrough (for example, through a hole 322 in the mirror, or a transparent portion of the mirror, or the like). In some alternative implementations, the reflector 320 comprises a beamcombiner or beamsplitter, which transmits some light and reflects some light. This beamsplitter may, for example, transmit light reflected from the patent's eye 170. Other designs are possible. The reflector 320 may be disposed in the second optical path between lens 330 and lens 310, which shown in the second optical path between the reflector and the detector array 380. Light reflected from the eye 170 that passes through reflector 320 can optionally pass through a lens 310 to the detector array 380. In some implementations, lens 310 can include one or more lenses. In the design shown in FIG. 3, lens 310 includes a plurality of lenses, which are illustrated as arranged on a lens wheel and positioned between the reflector 320 and the detector array 380. Lens wheel can be controlled by a motor driver which may, in some designs, be controlled by electronics 210. The lens wheel can permit different of the plurality of lenses in the lens wheel to be selected to provide different optical arrangements and/or optical different optical performance, for example, different amounts of zoom or magnification. Lens 310 can include additional lens elements as shown in FIG. 3 where an additional lens element is disposed between the lens wheel and detector array 380. Lens 310, for example, the combination of one of the lens elements in the lens wheel and the lens element between the lens wheel and the detector array 380, can focus the light on the detector array, possibly providing adjustable zoom and/or magnification via selection of different lens elements in the lens wheel. Selection of a suitable lens can be performed via the optics control 116 in some designs.

Light reflected from the eye 170, for example, from the retina, can be directed onto a detector array 380, which may comprise one or more image sensors (such as, charge-coupled devices or CCDs). Detector array 380 can convert light into one or more electrical signals that represent the captured image of the retina. Detector array 380 can provide one or more electrical signals to electronics 210. For example, serial interface (such as, Camera Serial Interface or CSI) can be used to communicate data between the detector array 380 and electronics 210. In some cases, an analog-to-digital controller (ADC) can transform one or more electrical signals from analog to digital form for processing by electronics 210. The at least one image can be processed by a digital signal processor (DSP), for instance, to increase signal-to-noise ratio (SNR), filter out noise, or the like. In some cases, linear or cubic interpolation can be used to smooth the at least one image. Other processing may be performed alternatively or in addition. The at least one image can be one or more of displayed on the display 130 or stored in the storage 224.

Image detection system 300 can optionally support autofocus. In some implementations, a motor driver, for example, can move one or more lenses (such as, one or more lenses 360, 340, 330, or 310) or the detector array 380 (or image sensor), for example, in a longitudinal direction along the direction of the first and/or second optical paths, to adjust the focus. In some cases, one or more autofocus sensors (not shown) can be configured to sense reflected light and facilitate autofocus using phase detection or other possible methods. In certain cases, contrast detection is used for autofocus. Contrast detection can be used to adjust focus until intensity of reflected light sensed by the detector array 380 and/or image contrast has been sufficiently increased or possibly maximized. Additionally or alternatively, image sharpness can be used for autofocus. In some designs, the user can select a region of the image (for example, using a touch screen display 130) to focus on. In some instances, contrast detection utilizes edge detection, which can involve adjusting the focus until dark lines have a sufficiently reduced, possibly a minimal amount of any one or more of blur, thickness, distortion. Another feature may be used to determine the level of focus. Other approaches may be employed.

Disease Identification

Electronics (or electronic processing circuitry) 210 can include one or more controllers or processors configured to analyze one or more images to identify a disease. For example, electronics 210 can include a processing system (such as, a Jetson Nano processing system manufactured by NVIDIA or a Coral processing system manufactured by Google), a System-on-Chip (SoC), or a Field-Programmable Gate Array (FPGA) to analyze one or more images. One or more images (or photographs) can be captured, for example, by the user operating the camera control 114 and stored in the storage 224. One or more prompts can be output on the display 130 to guide the user (such as, "Would you like to capture an image?" or "Capture an image of the right eye first."). Additionally or alternatively, symbols and graphics may be output on the display 130 to guide the user. Image quality can be verified before storing the image in the storage 224. Image quality may be determined automatically (for example, by the AI system or other software or firmware) and/or manually (for example, by the user). If any of the images is determined to be of poor quality (for instance, as compared to a quality threshold), the user can be notified, the user may be guided to retake the image, the image may be tagged as poor quality, the image may not be stored, or the like. Image quality can be determined based on one or more of brightness, sharpness, contrast, color accuracy, distortion, noise, dynamic range, tone reproduction, or the like. Image quality may also be determined by a deep learning machine learning model that has been trained to detect poor quality images.

One or more preset modes can facilitate easy and efficient capture of multiple images. Such one or more preset modes can automatically focus, capture one or more images, verify image quality, and store one or more images. For some designs the one or more preset modes can switch one or more settings (such as, switch the light source 302 to infrared light), and repeat this cycle without user intervention. In some designs, for example, a preset mode can facilitate obtaining multiple images for subsequent analysis. Such multiple images, for example, can be taken from different angles or capture different sections of the anatomy (for instance, retina), use different light sources, or the like. This feature can facilitate automatically collecting an image set for the patient. In some cases, the image or images may be automatically evaluated for image quality and the presence of disease. For example, a preset mode can capture one or more images, automatically assess image quality of the one or more images, automatically store the one or more images, automatically evaluate the one or more images for the presence of disease, and output the results on the display.

The user can select a region of an image for analysis, for instance, by outlining the region on the touch screen display 130, zooming in on region of interest on the display 130, or the like. In some cases, by default the entire image may be analyzed.

One or more machine learning models can be used to analyze one or more images. One or more machine learning models can be trained using training data that includes images of subjects having various diseases of interest, such as retina disease (retinopathy, macular degeneration, macular hole, retinal tear, retinal detachment, or the like), ocular disease (cataracts or the like), systemic disease (diabetes, hypertension, or the like), Alzheimer's disease, etc. For example, any of the machine learning models can include a convolutional neural network (CNN), decision tree, support vector machine (SVM), regressions, random forest, or the like. One or more machine learning models can be trained to determine the presence of one or more diseases. Training of one or more models can be performed using many annotated images (such as, thousands of images, tens of thousands of images, hundreds of thousands of images, or the like). Training of one or more models may be performed external to the retina camera 100. Parameters of trained one or more machine learning models (such as, weights) can be transferred to the retina camera, for example, via retina camera's wireless or wired interface 222 (such as, a USB interface). Parameters of one or more models can be stored in the storage 224 (or in another memory of electronics 210). Output of the analysis (sometimes referred to as a diagnostic report) can include one or more of determination of the presence of disease(s), severity of disease(s), character of disease(s), clinical recommendation(s) based on the likelihood of presence or absence of disease(s). A diagnostic report can be displayed on the display 130 and/or stored on the device (such as, in the storage 224). The diagnostic report can be stored in electronic medical record (EMR) format, such as EPIC EMR, or an alternate format, such as portable document format (PDF). The diagnostic report can be transmitted to a computing device (such as, a server). In some cases, the diagnostic report but not image data can be transmitted to the computing device, which can facilitate compliance with applicable medical records regulations (such as, HIPPA, GDPR, or the like). In some instances, the diagnostic report may include image data.

One or more machine learning models can determine the presence of a disease based on the output of one or more models. As described herein, images can be analyzed by one or more machine learning models one at a time or in groups to determine presence of the disease. When images are analyzed one at a time, determination of presence of the disease can be made in response to output of one or more models. When images are analyzed in a group, determination of presence of the disease can be made in response to combined outputs of one or more models analyzing the group of images.

The user can provide information (or one or more tags) to increase accuracy of the analysis by one or more machine learning models. For example, the user can identify any relevant conditions, symptoms, or the like that the patient (and/or one or more patient's family members) has been diagnosed with or has experienced. Relevant conditions can include systemic disease, retinal disease, ocular disease, or the like. Relevant symptoms can include blurry vision, vision loss, headache, or the like. Symptom timing, severity, or the like can be included in the identification. The user can provide such information using one or more user interface components on the display 130, such as a drop-down list or menu. One or more tags can be stored along with one or more pertinent images in the storage 224. One or more tags can be used during analysis by one or more machine learning models during analysis and evaluation. One or more images along with one or more tags can be used as training data.

Figure 4:
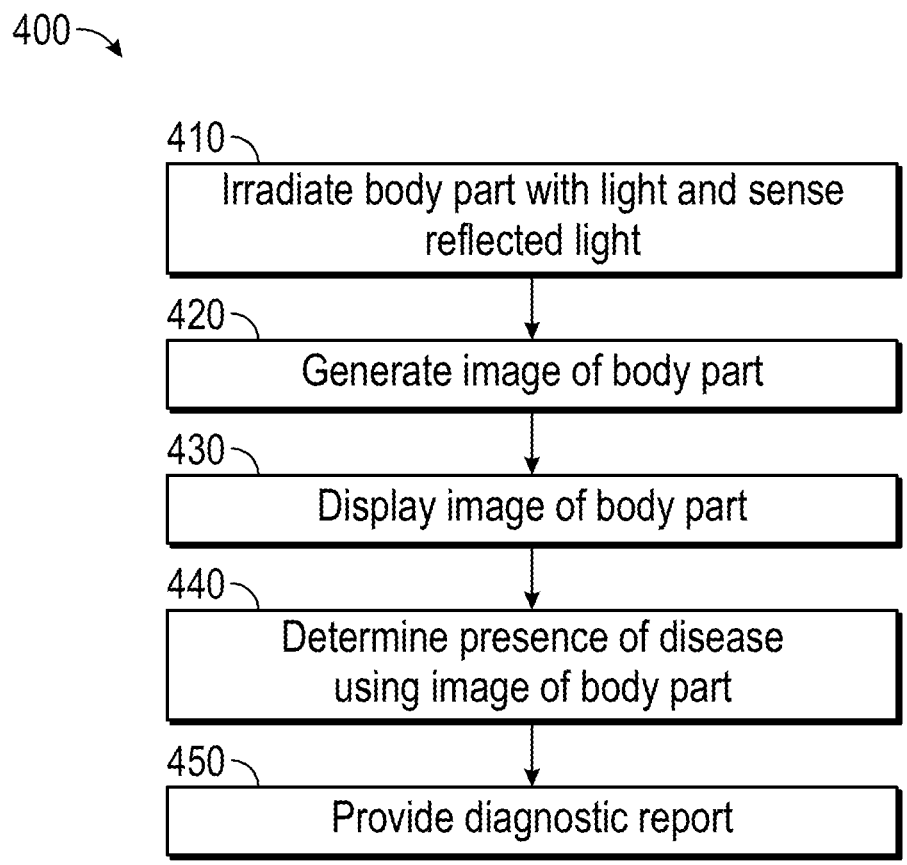
FIG. 4 illustrates a flow chart of a process for operating the retina camera of FIG. 1.

FIG. 4 illustrates a flow chart of a process 400 for operating the retina camera 100. The process 400 can be implemented by one or more components of the retina camera 100, such as by electronics 210 alone or in combination with the image detection system 300. In block 410, the process 400 can irradiate the patient's eye with light and sense reflected light. In block 420, the process 400 can generate an image of the patient's eye based on the sensed light. In block 430, the process 400 can display the image. In block 440, the process 400 can analyze the image to detect the presence of a disease. In block 450, the process 400 can provide a diagnostic report or report providing a likelihood of disease assessment and/or of disease risk factors that includes results of the analysis. In some cases, the diagnostic report may alternatively or additionally provide information indicating increased risk of disease or condition for a physician's (such as, ophthalmologist's) consideration. Physician can use this information during subsequent evaluation of the patient. For example, the physician can perform further testing to determine if one or more diseases are present.

Image analysis, including the application of one or more machine learning models to one or more images, can be performed by execution of program instructions by a processor (such as, Jetson Nano) and/or by a specialized integrated circuit that implements the machine learning model in hardware.

Disclosed devices and methods can, among other things, make the process of retinal assessment comfortable, easy, efficient, and accurate. Disclosed devices and methods can be used in physician offices, clinics, emergency departments, hospitals, in telemedicine setting, or elsewhere. Unnecessary visits to a specialist healthcare provider (such as, ophthalmologist) can be avoided, and more accurate decisions to visit a specialist healthcare provider can be facilitated. In places where technological infrastructure (such as, network connectivity) is lacking, disclosed devices and methods can be used because connectivity is not needed to perform the assessment.

Other Variations

Although the foregoing provides one or more examples of a retina camera, disclosed systems, devices, and methods are not limited to retina cameras, but can be extended to any diagnostics device, such as an otoscope, dermatology scope, or the like. Although the foregoing provides one or more examples of a portable medical diagnostics device, the approaches disclosed herein can be utilized by non-portable (such as, table top) diagnostics devices.

Additionally, the design may vary as components may be added, removed, or rearranged. For example, the image detection system 300 may comprise other arrangements or configurations. More or less optical elements (e.g., lens) may be employed and the location or arrangement of such elements may vary. Similarly, one or more different optical elements than those shown in FIG. 3 may be employed.

Any of the transmission of data described herein can be performed securely. For example, one or more of encryption, https protocol, secure VPN connection, error checking, confirmation of delivery, or the like can be utilized.

Although the foregoing provides one or more examples of live image or video analysis on-board, disclosed systems, devices, and methods are not so limited and can be utilized by cloud-based systems, particularly in situations where reliable network connectivity is available.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability of hardware and software, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electronic circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An example storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description.

All changes which come within the meaning and range of equivalency of the claims are to be embraced within their scope.

What is claimed is:

1. A retina camera comprising:
   a housing comprising a body and a handle, the handle connected to the body and configured to be held by a user;
   a display at least partially supported by the housing;
   a light source supported by the housing, the light source configured to irradiate an eye of a patient with light;
   imaging optics supported by the housing, the imaging optics configured to receive light reflected by the eye;
   an image detector array configured to receive light from the imaging optics and to sense the received light; and
   an electronic processing circuitry supported by the housing, the electronic processing circuitry configured to:
      generate at least one image of the eye based on signals received from the image detector array;
      display the at least one image on the display;
      process the at least one image with a machine learning model to determine presence of at least one disease from a plurality of diseases that the machine learning model has been trained to identify; and
      provide a determination of the presence of the at least one disease on the display,
   wherein the electronic processing circuitry processes the at least one image and provides the determination of the presence of the at least one disease without requiring network connectivity.

2. The retina camera of claim 1, wherein the electronic processing circuitry further comprises memory configured to store a plurality of parameters of the machine learning model.

3. The retina camera of claim 1, further comprising a cup configured to be positioned at a distal end of the body, the cup configured to be an interface between the housing and the eye of the patient.

4. The retina camera of claim 1, wherein the display comprises a touch screen display.

5. The retina camera of claim 4, wherein the electronic processing circuitry is configured to permit the user to select a region of the at least one image to be processed with the machine learning model using the touch screen display.

6. The retina camera of claim 1, wherein the imaging optics comprises autofocus optics.

7. The retina camera of claim 1, wherein the electronic processing circuitry is further configured to adjust at least one of zoom or focus of the imaging optics.

8. The retina camera of claim 1, wherein at least one of the imaging optics, image detector array, or the electronic processing circuitry is further configured to capture an image of the eye, and wherein the electronic processing circuitry is further configured to adjust at least one of zoom, aperture, or focus of at least one of the imaging optics or the image detector array used to capture the image.

9. The retina camera of claim 8, further comprising a user input supported by the handle, the user input configured to at least one of:
   adjust wavelength of light produced by the light source; or
   adjust at least one of the aperture, zoom, or focus of the imaging optics.

10. The retina camera of claim 9, wherein the user input comprises at least one of a button or a wheel.

11. The retina camera of claim 9, wherein adjusting the wavelength of light produced by the light source comprises selecting a first wavelength of light prior to capture of the at least one image and selecting a second wavelength of light for capture of the at least one image.

12. The retina camera of claim 1, wherein the electronic processing circuitry is further configured to receive at least one tag associated with the at least one image and store the at least one tag and the at least one image in memory, the at least one tag facilitating processing the at least one image with the machine learning model.

13. The retina camera of claim 12, wherein the at least one tag comprises information associated with at least one of a condition or symptom of the patient.

14. The retina camera of claim 1, wherein the machine learning model is at least one of: trained on a shallow neural network, comprises a depth-wise separable convolutional neural network, comprises a convolutional neural network in which one or more nodes or weights have been removed, or comprises a convolutional neural network in which one or more weights or activation layer parameters have been quantized.

15. A portable medical diagnostics instrument comprising:
   a housing comprising a body and a handle, the handle connected to the body and configured to be held by a user;
   a display at least partially supported by the housing;
   a light source supported by the housing, the light source configured to irradiate a body part of a patient with light;
   imaging optics supported by the housing, the imaging optics configured to receive light reflected by the body part;
   an image detector array configured to receive light from the imaging optics and to sense the received light; and
   an electronic processing circuitry supported by the housing, the electronic processing circuitry configured to:
      generate at least one image of the body part based on signals received from the image detector array;
      display the at least one image on the display;
      process the at least one image with a machine learning model to determine presence of at least one disease from a plurality of diseases that the machine learning model has been trained to identify; and
      provide a determination of the presence of the at least one disease on the display.

16. The portable medical diagnostics instrument of claim 15, wherein the body part comprises an eye of the patient, ear of the patient, or skin of the patient.

17. The portable medical diagnostics instrument of claim 15, wherein the display comprises a touch screen display, and wherein electronic processing circuitry is configured to permit the user to select a region of the at least one image to be processed with the machine learning model using the touch screen display.

18. The portable medical diagnostics instrument of claim 15, wherein at least one of the imaging optics, image detector array, or the electronic processing circuitry is further configured to capture an image of the body part, and wherein the electronic processing circuitry is further configured to adjust at least one of zoom, aperture, or focus of at least one of the imaging optics or the image detector array used to capture the image.

19. The portable medical diagnostics instrument of claim 15, wherein the electronic processing circuitry is further configured to receive at least one tag associated with the at least one image and store the at least one tag and the at least one image in memory, the at least one tag facilitating processing the at least one image with the machine learning model, the at least one tag comprising information associated with at least one of a condition or symptom of the patient.

20. The portable medical diagnostics instrument of claim 15, wherein the machine learning model is at least one of: trained on a shallow neural network, comprises a depth-wise separable convolutional neural network, comprises a convolutional neural network in which one or more nodes or weights have been removed, or comprises a convolutional neural network in which one or more weights or activation layer parameters have been quantized.

21. A method of diagnosing a patient using a portable medical diagnostics instrument, the method comprising:
  by an electronic processing circuitry of the portable medical diagnostics instrument:
    generating at least one image of a body part of a patient based on signals received from an image detector array of the portable medical diagnostics instrument responsive to sensing light reflected by the body part subsequent to irradiating the body part with light;
    displaying the at least one image on a display of the portable medical diagnostics instrument;
    processing the at least one image with a machine learning model to determine presence of at least one disease from a plurality of diseases that the machine learning model has been trained to identify; and
    providing a determination of the presence of the at least one disease on the display.

* * * * *

UNITED STATES PATENT AND TRADEMARK OFFICE
CERTIFICATE OF CORRECTION

PATENT NO. : 11,950,847 B1
APPLICATION NO. : 17/211166
DATED : April 9, 2024
INVENTOR(S) : Luke Michael Moretti et al.

Page 1 of 1

It is certified that error appears in the above-identified patent and that said Letters Patent is hereby corrected as shown below:

On the Title Page

Item (73), (Assignee), Line 1 (Name of Assignee), delete "Al" and insert -- AI --.

Page 2, Column 1 Item (56), (Other Publications), Line 1, delete "Gianose" and insert -- Diagnose --.

In the Drawings

Sheet 3 of 4 (FIG. 3), Line 6 (approx.), delete "Patinent" and insert -- Patient --.

In the Specification

Col. 2, Line 11, delete "connectivity" and insert -- connectivity. --.

Signed and Sealed this
Seventeenth Day of September, 2024

Katherine Kelly Vidal
*Director of the United States Patent and Trademark Office*